United States Patent
Wittnebel (10) Patent No.: US 11,033,185 B2
(45) Date of Patent: Jun. 15, 2021

(54) SYSTEM AND METHOD FOR AUTOMATIC TORSION CORRECTION IN DIAGNOSTIC OPHTHALMIC MEASUREMENTS

(71) Applicant: ALCON INC., Fribourg (CH)

(72) Inventor: Michael Wittnebel, Hirschaid (DE)

(73) Assignee: Alcon Inc., Fribourg (CH)

( * ) Notice: Subject to any disclaimer, the term of this patent is extended or adjusted under 35 U.S.C. 154(b) by 208 days.

(21) Appl. No.: 16/428,546

(22) Filed: May 31, 2019

(65) Prior Publication Data

US 2019/0374099 A1 Dec. 12, 2019

Related U.S. Application Data (60) Provisional application No. 62/682,242, filed on Jun. 8, 2018.

(51) Int. Cl.
*A61B 3/00* (2006.01)
*G06T 7/00* (2017.01)

(52) U.S. Cl.
CPC .......... *A61B 3/0025* (2013.01); *A61B 3/0008* (2013.01); *G06T 7/0012* (2013.01); *G06T 2207/10004* (2013.01); *G06T 2207/10048* (2013.01); *G06T 2207/30041* (2013.01)

(58) Field of Classification Search
CPC ................ A61B 3/0008; A61B 3/0025; G02B 2027/0138; G02B 27/017; G02B 2027/014; G02B 2027/0187; G02B 27/0093; G06T 2207/10004; G06T 2207/10048; G06T 2207/30041; G06T 2207/30196; G06T 7/0012; G06T 7/60
See application file for complete search history.

(56) References Cited

U.S. PATENT DOCUMENTS

| | | |
|---|---|---|
| 2002/0097378 A1 | 7/2002 | Saito |
| 2003/0223037 A1 | 12/2003 | Chernyak |
| 2004/0044333 A1 | 3/2004 | Sugiura |
| 2005/0024586 A1 | 2/2005 | Teiwes |
| 2010/0057059 A1 | 3/2010 | Makino |
| 2017/0109580 A1* | 4/2017 | Kaehler ............... G02B 27/017 |
| 2017/0189233 A1 | 7/2017 | Dewey et al. |

* cited by examiner

*Primary Examiner* — Brandi N Thomas (57) ABSTRACT

The disclosure includes an automatic torsion correction system and method using a processor to access information regarding a first and a second infrared or white light image and a corresponding, concurrently captured first and second ophthalmic diagnostic image; identify ophthalmic features in the first infrared or white light image and the second infrared or white light image and use these features to determine a first torsion of the first infrared or white light image with respect to a vertical axis and a second torsion of the second infrared or white light image with respect to the vertical axis, then determine a first and a second torsion correction to align the first and second infrared or white light image with respect to the vertical axis and apply the first and second torsion corrections to the first and second ophthalmic diagnostic images, respectively, then send the corrected diagnostic images to a display.

20 Claims, 5 Drawing Sheets

SYSTEM AND METHOD FOR AUTOMATIC TORSION CORRECTION IN DIAGNOSTIC OPHTHALMIC MEASUREMENTS

TECHNICAL FIELD

The present disclosure provides systems and methods for automatic torsion correction of ophthalmic diagnostic images to provide aligned ophthalmic diagnostic images.

BACKGROUND

Diagnostic images of the eye are commonly captured using a variety of different instruments of ophthalmic diagnostic equipment. Although most such equipment includes devices, such as chin and forehead rests, to help the patient align the imaged eye in a roughly similar position for each image, distinct ophthalmic diagnostic images often present the eye in different vertical orientations, particularly if the ophthalmic diagnostic images are not taken at the same time or using the same instrument or type of ophthalmic diagnostic equipment. This makes it more difficult to interpret the information contained in the images in a combined manner that is helpful to the patient.

SUMMARY

The present disclosure includes an automatic torsion correction system. The system includes a processor having access to memory media storing instructions or sets of instructions executable by the processor to: access information regarding a first infrared or white light image and a corresponding, concurrently captured first ophthalmic diagnostic image; access information regarding a second infrared or white light image and a corresponding, concurrently captured second ophthalmic diagnostic image; identify at least two ophthalmic features in the first infrared or white light image and the second infrared or white light image; using the at least two ophthalmic features, determine a first torsion, if any, of the first infrared or white light image with respect to a vertical axis and a second torsion of the second infrared or white light image with respect to the vertical axis; if a first torsion exists, determine a first torsion correction to align the first infrared or white light image with respect to the vertical axis and apply the first torsion correction to the first ophthalmic diagnostic image; determine a second torsion correction to align the second infrared or white light image with respect to the vertical axis and apply the second torsion correction to the second ophthalmic diagnostic image; and send the first ophthalmic diagnostic image and the second ophthalmic diagnostic image to a display. The system also includes a display operable to display the first ophthalmic diagnostic image and the second ophthalmic diagnostic image.

The system may also include the following additional features, which may be used in combination with one another in any combinations and with any other features disclosed herein unless clearly mutually exclusive: i) the first ophthalmic diagnostic image and the second ophthalmic diagnostic image may be the same type of image; ii) the first ophthalmic diagnostic image and the second ophthalmic diagnostic image may be different types of images; iii) the first infrared or white light image and the second infrared or white light image may contain both infrared images and white light images; iv) the at least two ophthalmic features may include features of the sclera, limbus, or iris; v) using the at least two ophthalmic features to determine a first torsion, if any, and a second torsion may include comparing the color, size, shape, or relative locations of the two ophthalmic features; vi) the system may further include a first instrument of diagnostic equipment operable to concurrently capture the first infrared or white light image and the first ophthalmic diagnostic image and to generate the information regarding the first infrared or white light image and the first ophthalmic diagnostic image; vii) the first instrument of diagnostic equipment may be further operable to concurrently capture the second infrared or white light image and the second ophthalmic diagnostic image and to generate the information regarding the second infrared or white light image and the second ophthalmic diagnostic image; viii) the system may further include a second instrument of diagnostic equipment is operable to concurrently capture the second infrared or white light image and the second ophthalmic diagnostic image and to generate the information regarding the second infrared or white light image and the second ophthalmic diagnostic image; ix) the processor may be further operable to: access information regarding an additional infrared or white light image and a corresponding, concurrently captured additional ophthalmic diagnostic image; identify the at least two ophthalmic features in the additional infrared or white light image; determine an additional torsion correction to align the additional infrared or white light image with respect to the vertical axis and apply the additional torsion correction to the additional ophthalmic diagnostic image; and send the additional ophthalmic diagnostic image to a display; and the display may be further operable to display the additional ophthalmic diagnostic image.

The present disclosure also provides a method of automatic torsion correction using an automatic torsion correction system. The method includes: accessing information regarding a first infrared or white light image and a corresponding, concurrently captured first ophthalmic diagnostic image; accessing information regarding a second infrared or white light image and a corresponding, concurrently captured second ophthalmic diagnostic image; identifying at least two ophthalmic features in the first infrared or white light image and the second infrared or white light image; using the at least two ophthalmic features, determining a first torsion, if any, of the first infrared or white light image with respect to a vertical axis and a second torsion of the second infrared or white light image with respect to the vertical axis; if a first torsion exists, determining a first torsion correction to align the first infrared or white light image with respect to the vertical axis and applying the first torsion correction to the first ophthalmic diagnostic image; determining a second torsion correction to align the second infrared or white light image with respect to the vertical axis and applying the second torsion correction to the second ophthalmic diagnostic image; and displaying the first ophthalmic diagnostic image and the second ophthalmic diagnostic image.

The method may also include the following additional features, which may be used in combination with one another in any combinations and with any other features disclosed herein unless clearly mutually exclusive: i) the first ophthalmic diagnostic image and the second ophthalmic diagnostic image may be the same type of image; ii) the first ophthalmic diagnostic image and the second ophthalmic diagnostic image may be different types of images; iii) the first infrared or white light image and the second infrared or white light image may contain both infrared images and white light images; iv) the at least two ophthalmic features may include features of the sclera, limbus, or iris; v) using the at least two ophthalmic features to determine a first torsion, if any, and a second torsion may include comparing the color, size, shape, or relative locations of the two ophthalmic features; vi) the method may further include concurrently capturing, using a first instrument of diagnostic equipment, the first infrared or white light image and the first ophthalmic diagnostic image and generating the information regarding the first infrared or white light image and the first ophthalmic diagnostic image; vii) the method may further include concurrently capturing, using the first instrument of diagnostic equipment, the second infrared or white light image and the second ophthalmic diagnostic image and generating the information regarding the second infrared or white light image and the second ophthalmic diagnostic image; viii) the method may further include concurrently capturing, using thea second instrument of diagnostic equipment, the second infrared or white light image and the second ophthalmic diagnostic image and generating the information regarding the second infrared or white light image and the second ophthalmic diagnostic image; ix) the method may further include: accessing information regarding an additional infrared or white light image and a corresponding, concurrently captured additional ophthalmic diagnostic image; identifying the at least two ophthalmic features in the additional infrared or white light image; determining an additional torsion correction to align the additional infrared or white light image with respect to the vertical axis and applying the additional torsion correction to the additional ophthalmic diagnostic image; and displaying the additional ophthalmic diagnostic image.

BRIEF DESCRIPTION OF THE FIGURES

For a more complete understanding of the present disclosure and its features and advantages, reference is now made to the following description, taken in conjunction with the accompanying drawings, in which like numerals represent like elements, and in which.

DETAILED DESCRIPTION

The present disclosure provides systems and methods for automatic torsion correction of ophthalmic diagnostic images to provide aligned ophthalmic diagnostic images. Automatic correction is achieved by using infrared or white light images of the eye that are obtained concurrently with the ophthalmic diagnostic images.

Ophthalmic features in the infrared or white light images are automatically identified by the system so that the torsion of the two different infrared or white light images with respect to a vertical axis may be compared and a correction torsion to place both infrared or white light images in the same alignment with respect to a vertical axis may be calculated. The correction torsion may then be automatically applied to the corresponding ophthalmic diagnostic images so that the ophthalmic diagnostic images are also aligned with respect to the vertical axis.

Figure 1:
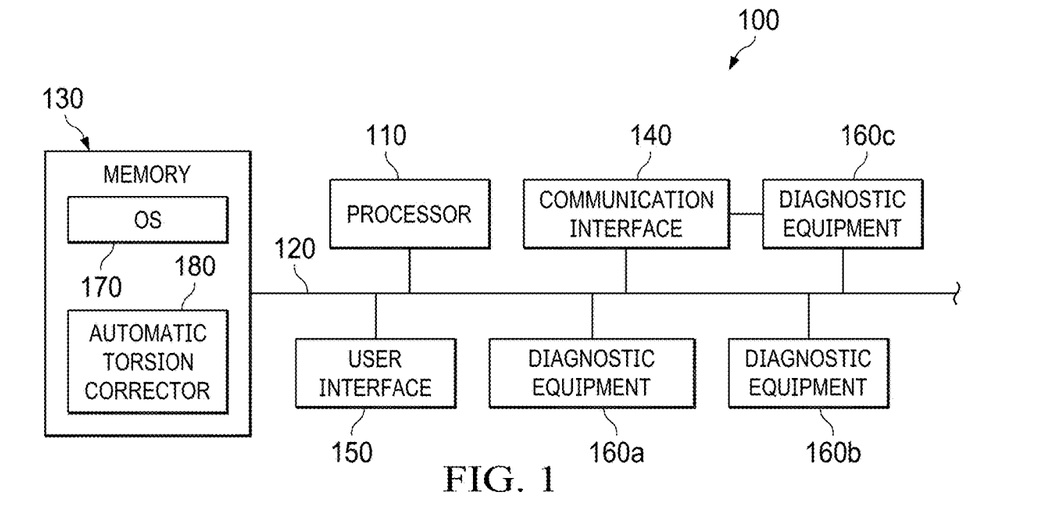
FIG. 1 is a block diagram of selected elements of a system for automatic torsion correction of ophthalmic diagnostic images to provide aligned ophthalmic diagnostic images.

Accordingly, the disclosure provides an automatic torsion correction system for automatic torsion correction of ophthalmic diagnostic images to provide aligned ophthalmic diagnostic images, such as system 100 in FIG. 1. An automatic torsion correction system according to the disclosure may include all of the elements of FIG. 1, but need not necessarily do so. An automatic torsion correction system may include any combinations of less than all of the elements represented in FIG. 1. For example, it may not include ophthalmic diagnostic equipment. In addition, any automatic torsion correction system may include additional elements not represented in FIG. 1, including, for example, additional diagnostic ophthalmic equipment.

The automatic torsion correction system 100 of FIG. 1, represented in block diagram form, includes a processor 110 coupled via a shared bus 120 to memory media collectively identified as the memory 130 and having access to such memory media. The automatic torsion correction system 100 further includes a communication interface 140 and a user interface 150, as well as diagnostic equipment 160a, 160b and 160c.

The processor 110 may be operable to execute instructions or sets of instructions stored in the memory 130.

The memory 130 may include persistent media, volatile media, or both, fixed media, removable media, or both, and magnetic media, semiconductor media, or both. Memory 130 is operable to store instructions, data, or both. The memory 130 as shown includes sets or sequences of instructions, namely an operating system 170 and automatic torsion corrector 180. The processor 110 may access information stored in the memory 130 via shared bus 120. It may also cause information to be stored in the memory 130. Processor 110 may also access information stored in memory of an ophthalmic diagnostic device 160 either through shared bus 120, typically if processor 110 is integrated with ophthalmic diagnostic device 160, or through communications interface 140, typically if processor 110 is separate from ophthalmic diagnostic device 160. Processor 110 may also access information stored in other memory (not shown) either through shared bus 120, typically if processor 110 is integrated with the other memory, or through communications interface 140, typically if processor 110 is separate from the other memory. Processor 110 may also cause information to be stored in the memory of the ophthalmic diagnostic device 160 or other memory.

The operating system 170 may be UNIX or UNIX-like operating system, a WINDOWS® (Microsoft Corporation, Washington, US) family operating system, or another suitable operating system.

The automatic torsion corrector 180 may include sets or sequences of instructions that, when executed by the processor 110, cause the automatic torsion correction system 100 to: automatically identify ophthalmic features in two different infrared or white light image; based upon those features, automatically compare torsion in the two different infrared or white light images with respect to a vertical axis; calculate a correction torsion to place both infrared or white light images in the same alignment with respect to a vertical axis; locate ophthalmic diagnostic images corresponding to the two different infrared or white light images; and apply the correction torsion to the corresponding ophthalmic diagnostic images so that the ophthalmic diagnostic images are also aligned with respect to the vertical axis.

The sets or sequences of instructions in automatic torsion corrector 180 may also, when executed by the processor 110, cause the automatic torsion correction system 100 to: access information regarding the infrared or white light images and their corresponding ophthalmic diagnostic images when such information is stored in memory 130, in the memory of a diagnostic device 160, or in other memory; cause information to be stored in memory 130, in the memory of the ophthalmic diagnostic device 160, or in other memory; cause one or more aligned diagnostic images to be displayed on user interface 150; or any combinations thereof.

The automatic torsion correction system 100 may include one or more instruments of ophthalmic diagnostic equipment, 160a, 160b, and 160c. One or more of instruments of the ophthalmic diagnostic equipment 160 (shown as the diagnostic equipment 160a and 160b in FIG. 1) may be integrated with the processor 110 and the memory 130, in which case the processor 110 or the memory 130, or both may communicate with the integrated ophthalmic diagnostic equipment 160 via the shared bus 120. Similarly, the other memory (not shown) may be integrated with processor 110 and memory 130, in which case the processor 110 or the memory 130, or both may communicate with the integrated other memory via the shared bus 120.

The communication interface 140 may be connected to the processor 110, the memory 130, or both via the shared bus 120. The communication interface 140 may allow the automatic torsion correction system 100 to connect to a network (not shown in FIG. 1) or to other equipment, particularly one or more instruments of the ophthalmic diagnostic equipment 160, if such equipment is not integrated with the processor 110 and the memory 130 (shown as the diagnostic equipment 160c in FIG. 1). The communication interface 140 may also allow the automatic torsion correction system 100 to connect to the other memory, if present and not integrated with the processor 110 and the memory 130.

The user interface 150 or a component thereof may be connected to the processor 110, the memory 130, or both via the shared bus 120 if integrated with the processor 110 and the memory 130, or via the communication interface 140 if not integrated with the processor 110 and the memory 130. The user interface 150 may accept commands from a user, display information to a user, or both. Commands may be input via a keyboard, mouse, touchpad, microphone, voice recognition interface, foot pedal, or other input devices, which may be part of the user interface 150. Information may be displayed on any device capable of displaying a still or video image, such as HD monitors, cathode ray tubes, projection screens, liquid crystal displays, organic light emitting diode displays, plasma display panels, light emitting diodes (LED) or organic LED (OLED), 3D equivalents thereof and the like, which may be part of the user interface 150.

The ophthalmic diagnostic equipment 160 may detect any of a number of eye properties. Each instrument of the ophthalmic diagnostic equipment 160 may be able to detect only one property, or each instrument may be able to detect two or more properties. As a result, the automatic torsion correction system 100 may be able to align different types of ophthalmic diagnostic images obtained using the same instrument, or different types of ophthalmic diagnostic images obtained using different instruments. Although FIG. 1 shows three instruments of the ophthalmic diagnostic equipment 160, the automatic torsion correction system 100 may be used with any number of instruments.

Eye properties detectable using the ophthalmic diagnostic equipment 160 may include topography, particularly corneal topography or lens front and back surface topography, wavefront mappings, pupil shape, corneal thickness, and subsurface features. Accordingly, the ophthalmic diagnostic equipment 160 may include a topolyzer, a wavefront analyzer, a pachymeter, a keratometer, a pupilometer, and an optical coherence tomography (OCT) device. Specific example devices include the Wavelight® Topolyzer (Novartis AG, Switzerland), the Wavelight® Topolyzer VARIO (Novartis AG), the Wavelight® ALLEGRO Oculyzer (Novartis AG), the Wavelight® ALLEGRO Oculyzer II (Novartis AG), the Wavelight® ALLEGRO Analyzer (Novartis AG), the Wavelight® ALLEGRO Analyzer II (Novartis AG), the CAPELLA™ Analyzer (Novartis AG), and the OCULUS Pentacam® AXL (Oculus, Inc., Washington, US).

The ophthalmic diagnostic equipment 160 may also include diagnostic equipment that is part of a therapeutic device. For example, it may include diagnostic equipment in a laser surgery or cataract surgery system. In particular, it may include diagnostic equipment in the Wavelight® EX500 (Novartis AG), the Wavelight® EX1000 (Novartis AG), the Wavelight® ALLEGRETTO WAVE EYE-Q (Novartis AG), the UV-FS™ System (Novartis, AG), the Wavelight® FS200 (Novartis AG), or a combination femtosecond and excimer laser system.

Each instrument of the diagnostic equipment 160 in the automatic torsion correction system 100 further includes a camera and, optionally, also a light source, for capturing an infrared or white light image of a patient's eye concurrently with the ophthalmic diagnostic image. Information representing this infrared or white light image is stored in a memory in such a way that it is associated with information representing the corresponding ophthalmic diagnostic image.

In the context of this disclosure, concurrently means within a sufficiently short time frame that the patient's eye would not normally have a different torsion with respect to a vertical axis in the infrared or white light image as compared to the ophthalmic diagnostic image, or any difference in torsion would normally be within an acceptable parameter, such as less than 0.5°, less than 0.25°, less than 0.1°, or less than 0.05°. A suitable time frame between capturing the infrared or white light image concurrently with the ophthalmic diagnostic image might include less than one second, less than 0.5 seconds, less than 0.1 seconds, less than 0.01 seconds. Concurrent capture of the infrared or white light image concurrently with the ophthalmic diagnostic image might be achieved by activating capture of both images using the same image capture signal.

Ophthalmic features identified in the infrared or white light images typically include at least two features, and may include many more, such as at least five features, at least ten features, or at least fifty features. Ophthalmic features in the iris of the eye may be particularly well-detected in infrared images, while ophthalmic features in the sclera of the eye may be particularly well-detected using white light images. The infrared or white light image may include both an infrared image and a white light image, and ophthalmic features may be detected using either or both infrared light or white light. Ophthalmic features include scleral vessels and limbus and iris features, such as darker spots. Ophthalmic features may be automatically identified by differences from surrounding tissue, such as differences in color. When ophthalmic features are used for automatic torsion correction, various properties of these features alone or in combination with one another may be used. Such properties include color, size, shape, and relative location.

The vertical axis may be defined with respect to the patient's eye whose properties are captured in the various images. Typically, the vertical axis will roughly correspond to vertical with the ground when the patient is sitting upright, but it can also be any single axis perpendicular to the apex of the cornea.

Torsion may be any measurable amount of torsion, such as between 0.5° and 355.5°, or between 1° and 359°.

Figure 2A:
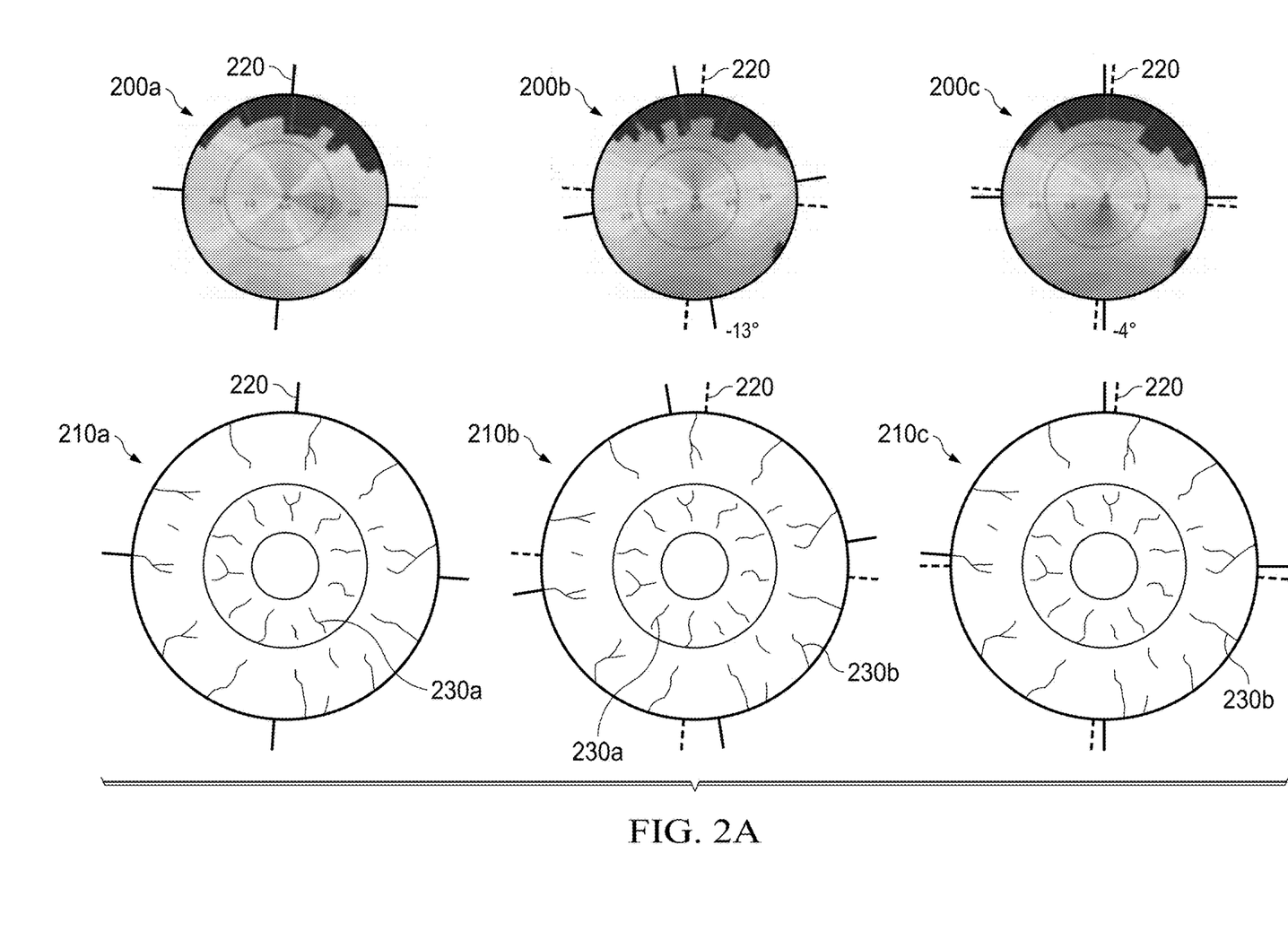
FIG. 2A is a diagram of three ophthalmic diagnostic topography images (top row) and three schematic ophthalmic infrared or white light images (bottom row) in which the eye is in a different torsional position in each image; each ophthalmic diagnostic topography image and the schematic infrared or white light image taken concurrently are in the same column.
Figure 2B:
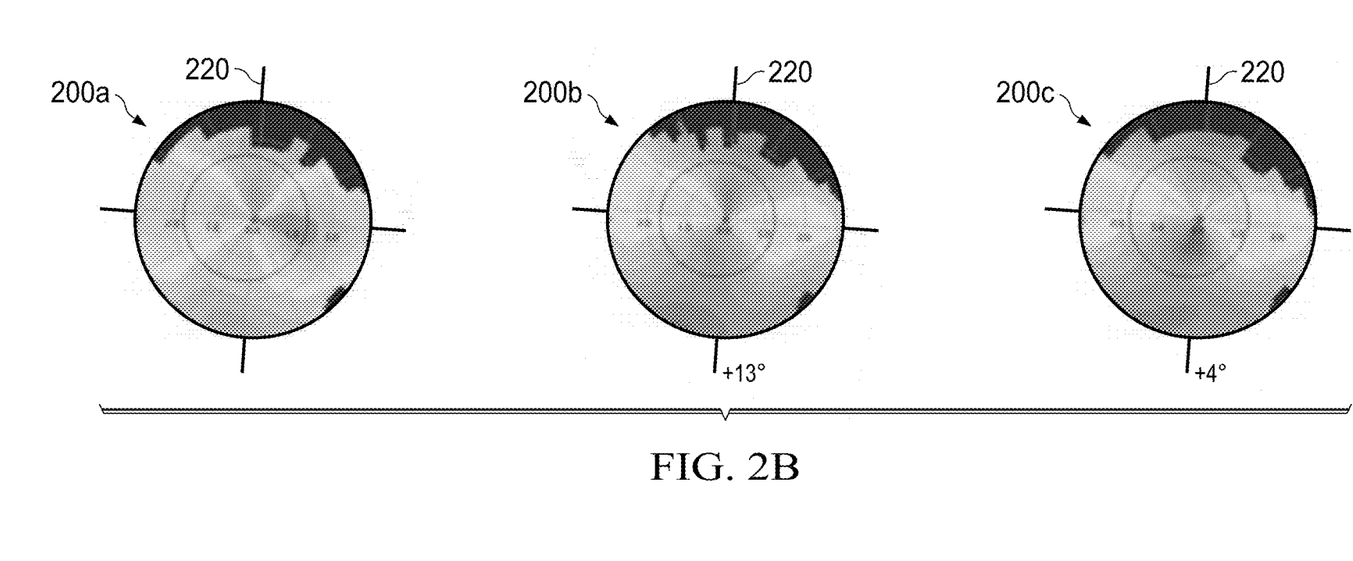
FIG. 2B is a diagram of the same three ophthalmic diagnostic topography images of FIG. 2A after they have been aligned using the infrared or white light images and automatic torsion correction.

By way of example, the automatic torsion correction system may access three ophthalmic diagnostic topography images, 200a, 200b, and 200c, as shown in the first row of FIG. 2A and their corresponding infrared or white light images, 210a, 210b, and 210c as shown below in the second row of FIG. 2A. In images 200a and 210a, the eye is aligned with the vertical axis 220. In images 200b and 210b, the eye has a torsion of −13° with respect to the vertical axis 220. In images 200c and 210c, the eye has a torsion of −4° with respect to the vertical axis 220. The eye contains ophthalmic features 230a in the iris and ophthalmic features 230b in the sclera, which may be used to automatically correct torsion in ophthalmic diagnostic topography images 200b and 200c. After automatic torsion correction, all of the ophthalmic diagnostic topography images 200a, 200b, and 200c have the same torsion with respect to the vertical axis 220 and are aligned with respect to the vertical axis 220. This makes comparison of the images easier for the user.

Figure 3A:
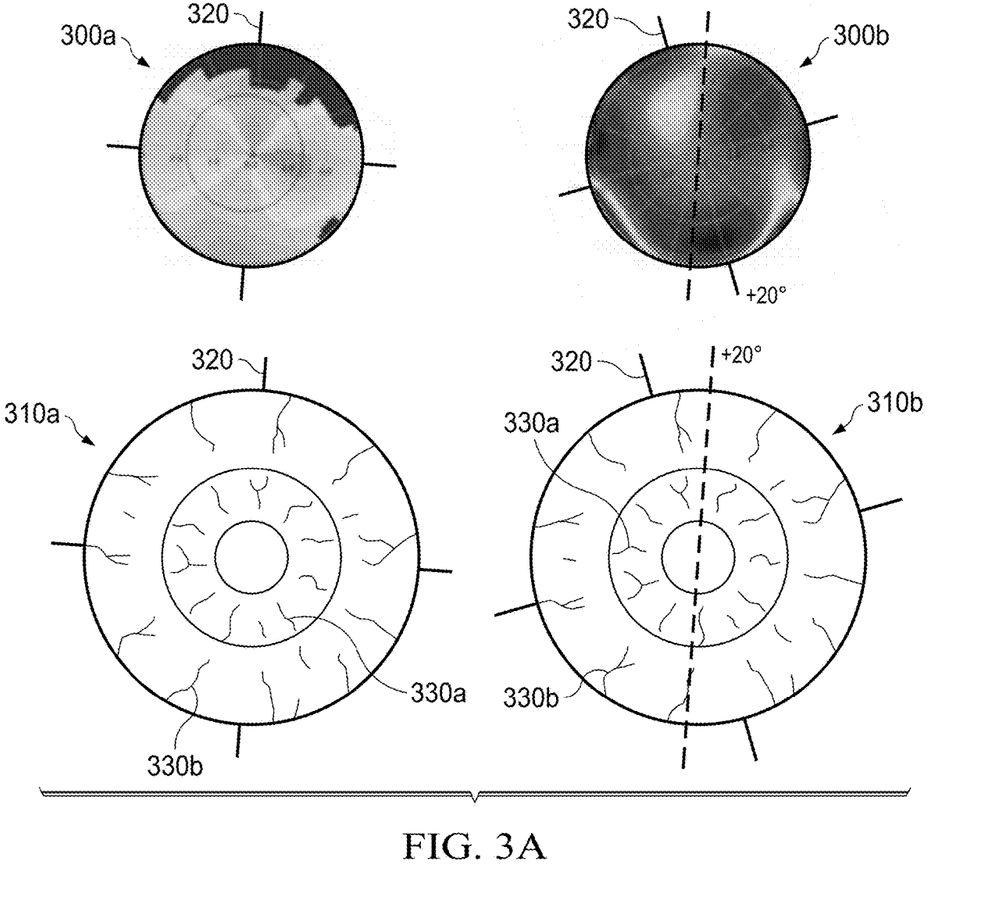
FIG. 3A is a diagram of an ophthalmic diagnostic topography image (top row, left column), a schematic infrared or white light obtained concurrently with the ophthalmic diagnostic topography image (bottom row, left column), an ophthalmic diagnostic wavefront image (top row, right column), and a schematic infrared or white light obtained concurrently with the ophthalmic diagnostic wavefront image (bottom row, right column)
Figure 3B:
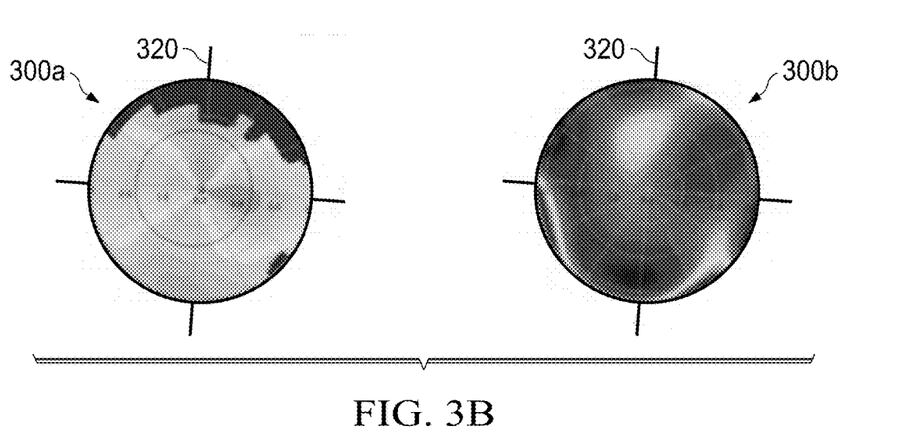
FIG. 3B is a diagram of the same two ophthalmic diagnostic images of FIG. 3A after they have been aligned using the infrared or white light images and automatic torsion correction.

By way of another example, the automatic torsion correction system may access an ophthalmic diagnostic topography image 300a, shown in the first row, left column of FIG. 3A, and its corresponding infrared or white light image 310a, shown in the second row, left column of FIG. 3A. The automatic torsion correction system may also access an ophthalmic diagnostic wavefront image 300b and its corresponding infrared or white light image 310b. In images 300a and 310a, the eye is aligned with the vertical axis 320. In images 300b and 310b, the eye has a torsion of +20° with respect to the vertical axis 230. The eye contains ophthalmic features 330a in the iris and ophthalmic features 330b in the sclera, which may be used to automatically correct torsion in ophthalmic diagnostic topography image 300b. After automatic torsion correction, both of the ophthalmic diagnostic topography images 300a and 300b have the same torsion with respect to the vertical axis 320 and are aligned with respect to the vertical axis 320. This makes comparison of the images, including the different types of data obtained via topography and wavefront analysis, easier for the user.

Figure 4:
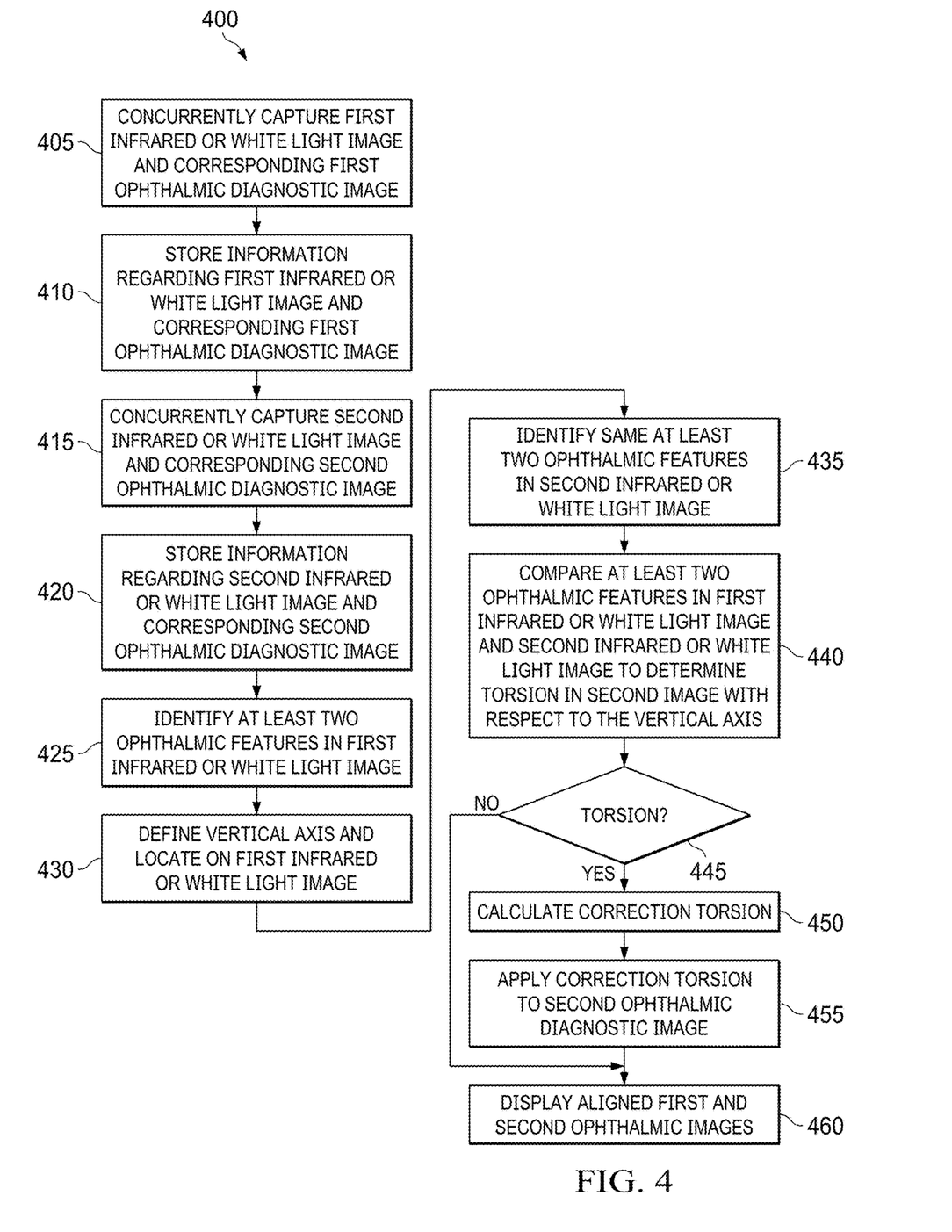
FIG. 4 is a flow chart of selected elements of a method of automatically correcting torsion in diagnostic ophthalmic images.

The present disclosure further provides a method of automatic torsion corrections such as the automatic torsion correction method 400 of FIG. 4. The above automatic torsion correction system 100 may implement all or part of the steps of the method. The method may be implemented automatically by an automatic torsion correction system, such as the automatic torsion correction system 100. An automatic torsion correction method according to the disclosure may include all of the steps of FIG. 4, but need not necessarily do so. An automatic torsion correction method may include any combinations of less than all of the steps represented in FIG. 4, provided that the steps are implemented in a workable order. In addition, any automatic torsion correction method may include additional steps not represented in FIG. 4.

All automatic torsion correction method steps described herein may also be implemented as a use of all automatic torsion correction systems described herein.

In automatic torsion correction method 400, in a first step 405, an instrument of diagnostic equipment concurrently captures a first infrared or white light image of an eye and a corresponding first ophthalmic diagnostic image of the eye.

In step 410, information regarding the first infrared or white light image and the corresponding first ophthalmic diagnostic image is stored in a memory.

In step 415, an instrument of diagnostic equipment concurrently captures a second infrared or white light image of the same eye. The instrument of diagnostic equipment may be the same as that of step 405, or different. Regardless of whether the instrument is the same or different, the first ophthalmic diagnostic image may be the same type of image as the second ophthalmic diagnostic image, or a different type of image.

In step 420, information regarding the second infrared or white light image and the corresponding second ophthalmic diagnostic image is stored in a memory.

In step 425, at least two ophthalmic features are identified in the first infrared or white light image.

In step 430, a vertical axis is defined for the eye and located on the first infrared or white light image.

In step 435, the same at least two ophthalmic features from step 425 are identified in the second infrared or white light image.

In step 440, at least two ophthalmic features in the first infrared or white light image are compared to the same at least two ophthalmic features in the second infrared or white light image to determine torsion if the second infrared or white light image exhibits torsion with respect to the vertical axis.

In step 445, if torsion is not detected, then no correction is made and the method proceeds to step 460.

In step 445, if torsion is detected, then in step 450 a correction torsion to place the first and second infrared or white light images in the same alignment with respect to a vertical axis is calculated.

In step 455, the correction torsion is applied to the second ophthalmic diagnostic image so that the first and second ophthalmic diagnostic images are aligned with respect to the vertical axis.

In step 460, the aligned ophthalmic diagnostic images are displayed.

The above method may include further steps, such as additional iterations of image capture and alignment and storage the aligned images in memory. The above method may also include variations, such as calculating a correction torsion for both the first and second ophthalmic diagnostic images if the vertical axis is defined such that both exhibit torsion with respect to it.

The invention claimed is:

1. An automatic torsion correction system, the system comprising:

a processor having access to memory media storing instructions or sets of instructions executable by the processor to:
  access information regarding a first infrared or white light image and a corresponding, concurrently captured first ophthalmic diagnostic image;
  access information regarding a second infrared or white light image and a corresponding, concurrently captured second ophthalmic diagnostic image;
  identify at least two ophthalmic features in the first infrared or white light image and the second infrared or white light image;
  using the at least two ophthalmic features, determine a first torsion, if any, of the first infrared or white light image with respect to a vertical axis and a second torsion of the second infrared or white light image with respect to the vertical axis;
  if a first torsion exists, determine a first torsion correction to align the first infrared or white light image with respect to the vertical axis and apply the first torsion correction to the first ophthalmic diagnostic image;
  determine a second torsion correction to align the second infrared or white light image with respect to the vertical axis and apply the second torsion correction to the second ophthalmic diagnostic image; and
  send the first ophthalmic diagnostic image and the second ophthalmic diagnostic image to a display; and
a display operable to display the first ophthalmic diagnostic image and the second ophthalmic diagnostic image.

2. The automatic torsion correction system of claim 1, wherein the first ophthalmic diagnostic image and the second ophthalmic diagnostic image are the same type of image.

3. The automatic torsion correction system of claim 1, wherein the first ophthalmic diagnostic image and the second ophthalmic diagnostic image are different types of images.

4. The automatic torsion correction system of claim 1, wherein the first infrared or white light image and the second infrared or white light image contain both infrared images and white light images.

5. The automatic torsion correction system of claim 1, wherein the at least two ophthalmic features include features of the sclera, limbus, or iris.

6. The automatic torsion correction system of claim 1, wherein using the at least two ophthalmic features to determine a first torsion, if any, and a second torsion comprises comparing the color, size, shape, or relative locations of the two ophthalmic features.

7. The automatic torsion correction system of claim 1, wherein the system further comprises a first instrument of diagnostic equipment operable to concurrently capture the first infrared or white light image and the first ophthalmic diagnostic image and to generate the information regarding the first infrared or white light image and the first ophthalmic diagnostic image.

8. The automatic torsion correction system of claim 7, wherein the first instrument of diagnostic equipment is further operable to concurrently capture the second infrared or white light image and the second ophthalmic diagnostic image and to generate the information regarding the second infrared or white light image and the second ophthalmic diagnostic image.

9. The automatic torsion correction system of claim 7, wherein the system further comprises a second instrument of diagnostic equipment is operable to concurrently capture the second infrared or white light image and the second ophthalmic diagnostic image and to generate the information regarding the second infrared or white light image and the second ophthalmic diagnostic image.

10. The automatic torsion correction system of claim 1, wherein the processor is further operable to:
  access information regarding an additional infrared or white light image and a corresponding, concurrently captured additional ophthalmic diagnostic image;
  identify the at least two ophthalmic features in the additional infrared or white light image;
  determine an additional torsion correction to align the additional infrared or white light image with respect to the vertical axis and apply the additional torsion correction to the additional ophthalmic diagnostic image; and
  send the additional ophthalmic diagnostic image to a display; and
wherein the display is further operable to display the additional ophthalmic diagnostic image.

11. A method of automatic torsion correction using an automatic torsion correction system, the method comprising:
  accessing information regarding a first infrared or white light image and a corresponding, concurrently captured first ophthalmic diagnostic image;
  accessing information regarding a second infrared or white light image and a corresponding, concurrently captured second ophthalmic diagnostic image;
  identifying at least two ophthalmic features in the first infrared or white light image and the second infrared or white light image;
  using the at least two ophthalmic features, determining a first torsion, if any, of the first infrared or white light image with respect to a vertical axis and a second torsion of the second infrared or white light image with respect to the vertical axis;
  if a first torsion exists, determining a first torsion correction to align the first infrared or white light image with respect to the vertical axis and applying the first torsion correction to the first ophthalmic diagnostic image;
  determining a second torsion correction to align the second infrared or white light image with respect to the vertical axis and applying the second torsion correction to the second ophthalmic diagnostic image; and
  displaying the first ophthalmic diagnostic image and the second ophthalmic diagnostic image.

12. The method of claim 11, wherein the first ophthalmic diagnostic image and the second ophthalmic diagnostic image are the same type of image.

13. The method of claim 11, wherein the first ophthalmic diagnostic image and the second ophthalmic diagnostic image are different types of images.

14. The method of claim 11, wherein the first infrared or white light image and the second infrared or white light image contain both infrared images and white light images.

15. The method of claim 11, wherein the at least two ophthalmic features include features of the sclera, limbus, or iris.

16. The automatic torsion correction system of claim 11, wherein using the at least two ophthalmic features to determine a first torsion, if any, and a second torsion comprises comparing the color, size, shape, or relative locations of the two ophthalmic features.

17. The method of claim 11, further comprising concurrently capturing, using a first instrument of diagnostic equipment, the first infrared or white light image and the first ophthalmic diagnostic image and generating the information regarding the first infrared or white light image and the first ophthalmic diagnostic image.

18. The method of claim 17, further comprising concurrently capturing, using the first instrument of diagnostic equipment, the second infrared or white light image and the second ophthalmic diagnostic image and generating the information regarding the second infrared or white light image and the second ophthalmic diagnostic image.

19. The method of claim 17, further comprising concurrently capturing, using thea second instrument of diagnostic equipment, the second infrared or white light image and the second ophthalmic diagnostic image and generating the information regarding the second infrared or white light image and the second ophthalmic diagnostic image.

20. The method of claim 11, further comprising:
   accessing information regarding an additional infrared or white light image and a corresponding, concurrently captured additional ophthalmic diagnostic image;
   identifying the at least two ophthalmic features in the additional infrared or white light image;
   determining an additional torsion correction to align the additional infrared or white light image with respect to the vertical axis and applying the additional torsion correction to the additional ophthalmic diagnostic image; and
   displaying the additional ophthalmic diagnostic image.

* * * * *